United States Patent [19]

Mano

[11] Patent Number: 4,713,070
[45] Date of Patent: * Dec. 15, 1987

[54] POROUS STRUCTURE OF POLYTETRAFLUOROETHYLENE AND PROCESS FOR PRODUCTION THEREOF

[75] Inventor: Hiroshi Mano, Osaka, Japan

[73] Assignee: Sumitom Electric Industries, Ltd., Osaka, Japan

[*] Notice: The portion of the term of this patent subsequent to Jun. 1, 1999 has been disclaimed.

[21] Appl. No.: 821,528

[22] Filed: Jan. 24, 1986

Related U.S. Application Data

[63] Continuation of Ser. No. 333,357, Dec. 22, 1981, abandoned, which is a continuation of Ser. No. 98,283, Nov. 28, 1979, Pat. No. 4,332,035.

[51] Int. Cl.$^4$ .......................... A61F 2/06; A61F 2/02
[52] U.S. Cl. .......................................... 623/1; 623/12; 623/66; 128/DIG. 14; 428/376
[58] Field of Search ............... 623/1, 12, 66; 428/376; 128/DIG. 14

[56] References Cited

U.S. PATENT DOCUMENTS

| | | | |
|---|---|---|---|
| 4,082,893 | 4/1978 | Okita | 428/376 |
| 4,193,138 | 3/1980 | Okita | 623/1 |
| 4,208,745 | 6/1980 | Okita | 623/1 |
| 4,229,838 | 10/1980 | Mano | 623/1 |
| 4,304,010 | 12/1981 | Mano | 623/1 |
| 4,332,035 | 6/1982 | Mano | 623/12 |

Primary Examiner—Richard J. Apley
Assistant Examiner—Alan W. Cannon
Attorney, Agent, or Firm—Sughrue, Mion, Zinn, Macpeak & Seas

[57] ABSTRACT

A porous polytetrafluoroethylene material is disclosed having a molecular microfibrous structure having, at one surface, a strong orientation in a given direction and, at another opposite surface, a strong orientation and a direction at right angles to the first, in which the orientation of the microfibrous structure progressively changes from one surface to the other. A process for preparing such an element is also disclosed.

11 Claims, 10 Drawing Figures

FIG.1
FIG.2
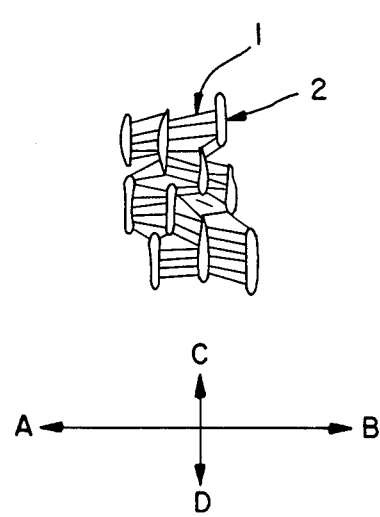
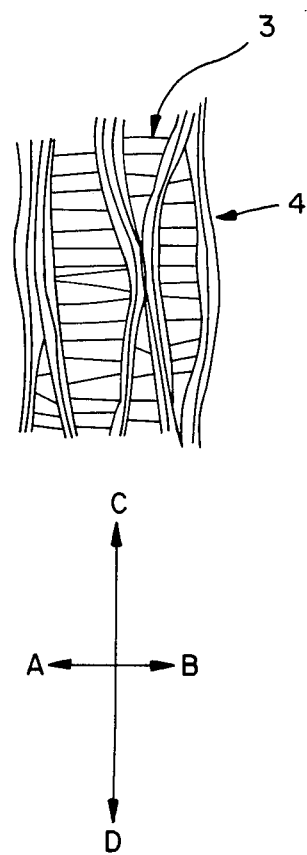

OUTSIDE SURFACE

X 200

OUTSIDE SURFACE

X 50

INSIDE SURFACE

X 200

CROSS SECTION

X 100

OUTSIDE SURFACE

X 200

OUTSIDE SURFACE

X 50

INSIDE SURFACE

X 200

CROSS SECTION

X 100

POROUS STRUCTURE OF POLYTETRAFLUOROETHYLENE AND PROCESS FOR PRODUCTION THEREOF

This is a continuation of application Ser. No. 333,357, filed Dec. 22, 1981, now abandoned, which is a continuation of application Ser. No. 098,283, filed Nov. 28, 1979, now U.S. Pat. No. 4,332,035.

BACKGROUND OF THE INVENTION

1. Field of the Invention

This invention relates to a porous structure of polytetrafluoroethylene (to be referred to as PTFE), and specifically, to a porous structure of PTFE having improved strength.

2. Description of the Prior Art

The porous PTFE structure is utilized in various fields for its excellent thermal stability, chemical resistance, electric insulation, non-tackiness, and lubricity. In particular, a porous PTFE structure produced by stretching has a microfibrous structure composed of very fine fibers and nodes connected to one another by these fibers. Because the pore diameter and porosity of the porous PTFE structure can be changed freely, it is expected to find a wide range of applications as filter materials such as a membrane filters, diaphragms, electrical insulating materials, materials for artificial organs (prostheses) such as an artificial vessels and artificial lungs, an endoscopic tube, etc.

However, since the porous PTFE structure is produced by stretching, the microfibrous structure of PTFE generated by the stretching is strongly oriented in the stretching direction, it has the defect of being readily torn along the stretching direction. Furthermore, the stretched porous PTFE structure has the defect that when a tensile force is applied thereto, the structure is strong in the stretching direction, but is susceptible to deformation at right angles to the stretching direction. In an attempt to remedy this defect, it has been suggested to lay two sheets of porous PTFE structure one over the other so that the stretching directions of the two cross each other at right angles and to bond the two sheets, or to wrap a stretched PTFE sheet about the outside surface of a porous PTFE tubing stretched in the axial direction.

It has now been found that a unitary porous structure of polytetrafluoroethylene can be produced in which the microfibrous structure has one surface having a strong orientation in one direction and another surface having a strong orientation in a direction at right angles to the aforesaid direction, the orientation of said microfibrous structure progressively changing from one surface to the other.

SUMMARY OF THE INVENTION

According to this invention, there is provided a unitary porous polytetrafluoroethylene structure having a microfibrous structure composed of fibers and nodes connected to one another by these fibers, the microfibrous structure including a portion having a strong orientation in one direction and a portion having a strong orientation in a direction at right angles to the aforesaid direction, the orientation of said microfibrous structure progressively changing from one of said portions to the other.

In another aspect, this invention provides a process for producing a porous structure of polytetrafluoroethylene, which comprises molding a mixture of an unsintered powder of polytetrafluoroethylene and a liquid lubricant into an article of the desired shape, stretching the molded article in at least one direction, and heating the molded porous article to a temperature above about 327° C. starting with a certain portion thereof while maintaining it in a condition capable of preventing its heat shrinkage, thereby to sinter it until the orientation of the microfibrous structure of that portion is larger in a direction at right angles to the directions of stretching than in the stretching direction.

DETAILED DESCRIPTION OF THE INVENTION

The porous PTFE structure in accordance with this invention is basically produced by the method described in Japanese Patent Publication No. 13560/67 and in U.S. Pat. Nos. 3,953,566 and 3,962,153 and U.S. application Ser. Nos. 760,789 (1/19/77) and 825,513 (8/17/77), and may have any desired form such as a sheet, tubing or rod. According to this method, an unsintered PTFE powder is mixed with a liquid lubricant. Suitable PTFE is commercially available and has a modular weight of about $10^6$ to $10^7$. The mixture is then extruded, and molded into the desired shape by rolling, etc. If desired, the liquid lubricant is then removed from the molded article by extraction, heat evaporation, etc. The molded product is stretched in at least one direction. While preventing heat shrinkage of the molded article, it is heated to a temperature above the sintering temperature (327° C.) to sinter it and set the stretched structure. Thus, a porous PTFE structure having increased strength can be obtained. "Preventing heat shrinkage", as used herein, means not only preventing shrinkage completely, but includes tolerable partial shrinkage.

The resulting porous structure of PTFE has a microfibrous structure composed of very fine fibers and nodes connected to one another by these fibers. Since the diameters and lengths of the fibers, and the sizes and number of the nodes can be varied depending upon the stretching and sintering conditions, the pore diameter and porosity of the resulting porous structure can be freely determined.

In the porous PTFE structure obtained by the aforesaid method, the fibrous structure of PTFE usually has a strong orientation in the stretching direction (the term "strong orientation" means more than half the fibers are oriented in that direction). It has been found, however, that when sintering is caused to proceed to a far greater extent than in ordinary sintering treatments in the sintering step in which the porous structure is heated to a temperature above 327° C., the fibrous structure of PTFE which initially has a strong orientation in the stretching direction is progressively oriented in a direction at right angles to the stretching direction, and finally attains an orientation in a direction at right angles to the direction of the initial orientation. This tendency is stronger as the porous PTFE structure is maintained at a higher temperature above 327° C. and for a longer period of time. However, heating is controlled such that the change in orientation of the fibers does not reach the opposite surface. The fibrous structure of PTFE can be heated by contacting it with the surface of a heated metal plate, rod, or the like, by blowing hot air, by contacting it with a heated liquid or heated fine powders while stirring, and like methods. The heated surface ultimately attains a network form having a pore diameter of several tens of μm to several mm. This change in the fibrous structure is believed to be due to breaking or melt-adhesion of the fine fibers and to the melt-adhesion of the nodes, and advances into the porous structure from the heated surface. It has been found therefore that by suitably selecting the sintering temperature and time, the fibrous structure has a progressively changing orientation in the porous structure ranging from a surface having a strong orientation in the stretching direction to a surface having a strong orientation in a direction at right angles to the stretching direction. Thus, the method in accordance with this invention is characterized by the fact that the porous PTFE structure has been sintered to a far greater extent than in an ordinary sintering of the porous PTFE structure.

BRIEF DESCRIPTION OF THE DRAWINGS

Referring to the accompanying drawings, explanation will be made of the change in the microfibrous structure of the porous polytetrafluoroethylene (PTFE) materials to demonstrate how the strong orientation of the microfibrous structure changes.

FIGS. 1 and 2 illustrate schematically, in a magnified scale, the portions having different directions of strong orientation. In FIG. 1, 1* is a fiber and 2* a node. In FIG. 2, 3* is a fiber and 4* a node. Arrows depicted below the respective figures indicate degree of strong orientation of microfibrous structure which is stronger in the direction of $\overline{AB}$ than that of $\overline{CD}$ in FIG. 1 and this relationship is reversed in FIG. 2.

In the present invention, the direction in which strong orientation of microfibrous structure is observed means a direction in which mechanical strength is increased. The feature of the present invention is that a part of the porous polytetrafluoroethylene material is rendered to have a structure illustrated in FIG. 2.

Usually, porous PTFE materials stretched in the direction of $\overline{AB}$ have a microfibrous structure as shown in FIG. 1. However, when the porous PTFE material is subjected to heat treatment until the direction in which strong orientation is observed is changed in some part of the porous PTFE material a number of nodes come to be combined to form a unitary node and minute fibers are cut partially, thus forming a microfibrous structure as illustrated in FIG. 2.

In the structure shown in FIG. 1, the strong orientation of microfibrous structure coincides the direction of stretching ($\overline{AB}$), i.e., the direction in which fibers extend, while it is shifted to the direction at right angles to the direction of $\overline{AB}$ in the structure shown in FIG. 2. This shift of direction proceeds from the surface on which heat has been applied towards the thickness direction. Thus, the porous PTFE material of the present invention has a portion in which strong orientation is observed in the direction wherein stretching has occurred in the largest amount and a portion in which strong orientation is present in the direction at right angles to that direction, which is the greatest feature of the present invention.

Figure 3:
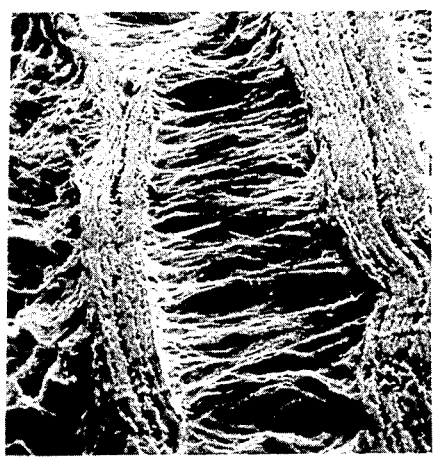
Figure 4:
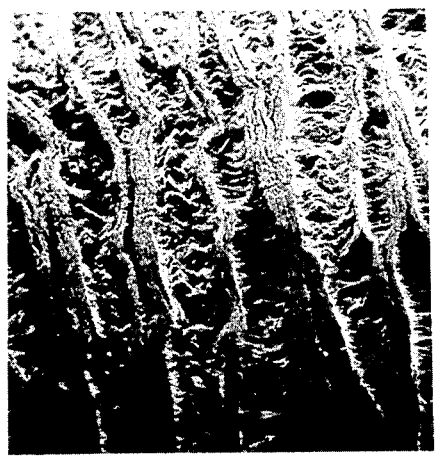
Figure 5:
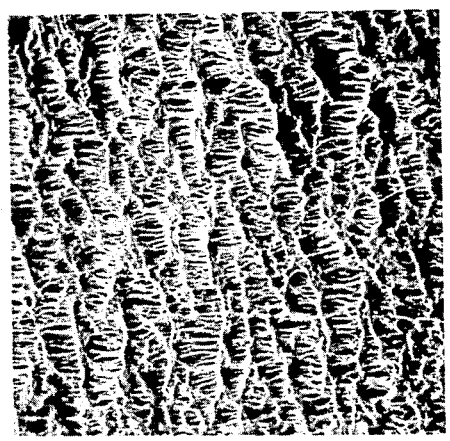
Figure 6:
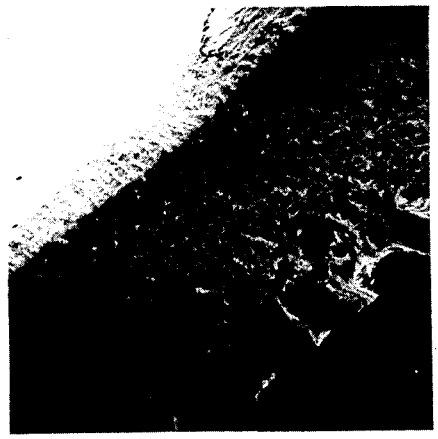

FIGS. 3, 4, 5 and 6 each represents a scanning electron micrograph of a porous PTFE tubing. FIG. 3 and FIG. 4 show outside surface of the tubing in a magnification of 200 and 50, respectively. FIG. 5 shows inside surface of the tubing in a magnification of 200. FIG. 6 is a cross-sectional view of the tubing in a magnification of 100.

The porous PTFE tubing of the present invention has a structure as shown in FIG. 1 on the inside surface thereof and a structure as shown in FIG. 2 on the outside surface thereof. It is apparent that on the outside surface microfibers are cut, The nodes become form a strong orientation around the axis of the tubing. This tube is very useful as vascular prosthesis.

Figure 7:
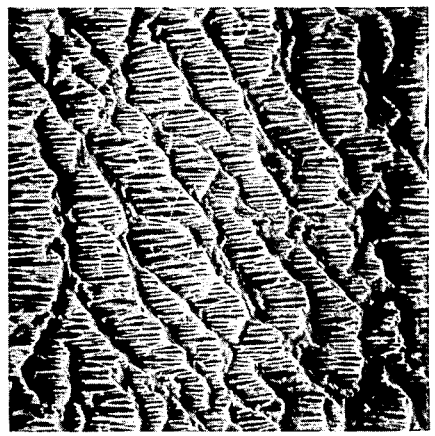
Figure 8:
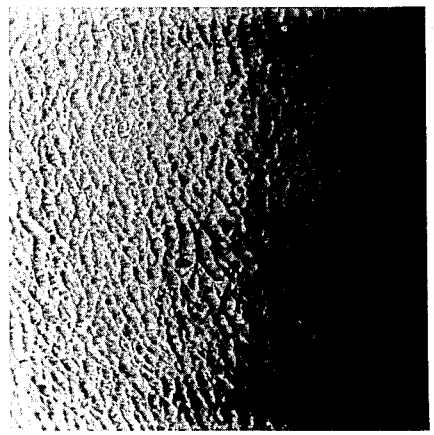
Figure 9:
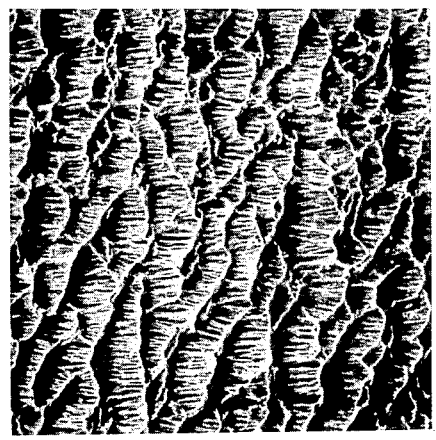
Figure 10:
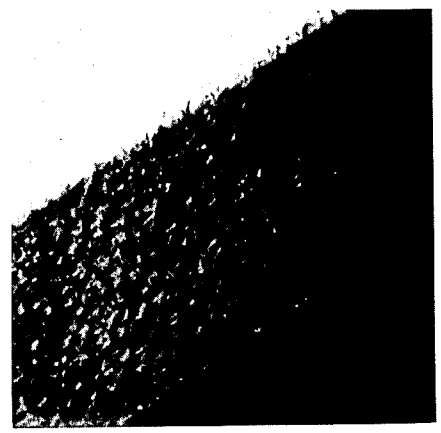

FIGS. 7, 8, 9 and 10 each represents a scanning electron micrograph of conventional porous PTFE tubing. FIG. 7 and FIG. 8 show the outside surface of the tubing in a magnification of 200 and 50, respectively. FIG. 9 shows the inside surface of the tubing in a magnification of 200. FIG. 10 is a cross-sectional view of the tubing in a magnification of 100. It is apparent both the inside and outside surfaces show a structure as shown in FIG. 1 and substantially uniform structure prevails throughout the tubing.

The present invention is described in further detail below with particular reference to an embodiment in which a porous tubing of PTFE suitable for a tubular organic prosthesis is obtained. The main purpose of applying the invention to tubular organic prostheses is to increase strength and to improve the ability of the prosthesis to connect with the tissues of a patient.

Many reports have been made heretofore to show that a porous tubing of PTFE produced by stretching can be clinically used as a tubular organic prosthesis, especially as a vascular prosthesis. Such a prosthesis is regarded as better than conventional prosthesis made of knitted or woven fabrics. A PTFE tubing which has been subjected to stretching treatment has a microfibrous structure composed of very fine fibers and nodes connected to one another by these fibers. The diameters of the fibers vary depending on stretching conditions, but can be made much smaller than those of the fibers of the knitted or woven fabrics mentioned above. Moreover, since the pore diameter and porosity of the tubing can be varied freely, when it is used, for example, as an artificial vessel, it is pliable and scarcely permits formation of thrombus. The tubing also shows good formation of a neointima on its inner surface without any appreciable adverse effect on the surrounding tissues. Thus, a stretched PTFE tubing is regarded as one of the best tubular organic prosthesis.

The stretched PTFE tubing, however, has the disadvantage that when it is used as a tubular organic prosthesis and joined with the living body, the needle or suture tends to tear the tubing. This tearing frequently occurs in the axial direction of the porous PTFE tubing, and is believed due to the strong orientation of fine PTFE fibers formed as a result of stretching. In an attempt to solve the problem of tube tearing, a unitary structure was suggested which comprises the porous PTFE tubing and helically wrapped around its outside surface, a porous tape of PTFE or fibers of another material. Such a structure is intended to prevent tearing in the axial direction by imparting to the outside surface of the tubing an orientation around the axis of the tubing. In contrast, the present invention provides a porous tubing of PTFE useful as a tubular organic prosthesis which is oriented in the axial direction and around the tube axis within the single tubing. In other words, the problem of tube tearing is solved by progressively changing the orientation of the microfibrous structure of the PTFE tubing ranging from its inside surface where there is a strong orientation in the axial direction of the tubing to its outside surface where there is a strong orientation around the axis of the tubing.

Furthermore, the conventional porous tubing of PTFE has the drawback that when it is sharply bent, the tubing buckles and cannot retain its cylindrical shape. In contrast, the porous PTFE tubing of this invention is resistant to buckling owing to the strong orientation of its outside surface around the axis of the tubing.

The conventional porous PTFE tubing also has the defect that when it is used as an organic prosthesis, its ability to connect with the surrounding tissues of a patient is low. In accordance with the present invention, the average pore diameter at outside surface of the tubing larger than that of the inner surface which permits easy entry and connection of the surrounding tissues of a patient to accelerate assimilation. When the porous PTFE tubing of this invention is used as a vascular prosthesis, its inside surface preferably has an average pore diameter of about 1 to 100 $\mu$m, and its outside surface should suitably have an average pore diameter of about 0.1 to 1.0 mm. It has been ascertained that pore diameters within these ranges can be easily obtained.

The porous PTFE tubing in accordance with this invention can also be used as prosthesis for other tubular organs including the esophagus, trachea, biliary duct, ureter and urethra.

As described in detail hereinabove, the porous PTFE structure of this invention has an increased utilitarian value because of its higher strength characteristics than the prior art.

The following Examples illustrate the present invention more specifically. It should be understood, however, that the scope of the invention is not limited by these Examples.

EXAMPLE 1

One hundred parts by weight of fine PTFE powder, Polyflon F-103 (a product of Daikin Kogyo Co., Ltd.), was mixed with 23 parts by weight of a white oil, a liquid lubricant, and they were mixed uniformly. The mixture was preliminarily press-formed, and then extruded and rolled into a sheet having a thickness of 0.5 mm. The sheet was dipped in trichloroethylene to extract the liquid lubricant, then stretched 100% monoaxially by a calender roll heated at about 275° C., and then stretched 200 % in the same direction by a calender roll heated at about 200° C.

The stretched sheet was contacted for 1 minute with a belt heated at about 520° C. to sinter it while preventing shrinkage thereof by driving a take up roll at the same speed as the supply speed of the stretched sheet after heating, and thus to obtain a porous PTFE sheet having a thickness of 0.37 mm, a porosity of 82%, and an average pore diameter of 5.0 $\mu$m. When the porous sheet of PTFE was contacted with the aforesaid heated belt with the opposite surface of the sheet being allowed to be air cooled for periods of 3 and 5 minutes, respectively, the heated surface had an average pore diameter of 80 $\mu$m, and 120 $\mu$m, respectively.

A stainless steel wire having a diameter of 0.4 mm was inserted through the porous sheet of PTFE at a position 5 mm from one end, and made into a loop form. The stainless steel loop was pulled at a speed of 50 mm/min in the stretching direction and in a direction perpendicular to it, and the loads at which tearing occurred in the sheet were determined. The load was 480 g in the stretching direction and 1,190 g in the perpendicular direction for the sheet sintered for 1 minute, 810 g in the stretching direction and 970 g in the perpendicular direction for the sheet sintered for 3 minutes, and 5,100 g in the stretching direction and 520 g in the perpendicular direction for the sheet sintered for 5 minutes, showing the reversing of the direction in which the orientation of the fibrous structure of the sheet was strong. It was found that a porous PTFE sheet having nearly equal strengths in both directions had superior strength characteristics and permeating characteristics for use as a membrane filter and an electrolytic diaphragm.

EXAMPLE 2

One hundred parts by weight of fine PTFE powder, Polyflon F-104E (a product of Daikin Kogyo Co., Ltd.), was mixed uniformly with 29 parts by weight of a liquid lubricant, DOSB (a product of Shell Chemical Co.). The mixture was preliminarily press-formed, and extruded into a tubing having an inside diameter of 3.0 mm and an outside diameter of 4.5 mm by a ram-type extruder. The tubing was dipped in trichloroethylene to extract the liquid lubricant, and stretched 300% in the axial direction at about 250° C. The stretched tubing was heated at about 330° C., and the pressure on the outside surface of the tubing was reduced to expand its inside diameter to 4.0 mm to form a porous tubing of PTFE. A stainless steel rod having a diameter of 4.0 mm was inserted in the tubing, and while fixing both ends thereof, it was heated by a hot air stream from the outside surface at 350° C. for 30 minutes. The stainless steel rod served to prevent shrinkage of the stretched tube and conduct heat of the inner surface to form thermal gradient. The tubing was cooled to room temperature, and then the stainless steel rod was withdrawn. Thus, a porous PTFE tubing was obtained which had an inside diameter of 4.0 mm, an outside diameter of 4.9 mm, a porosity of 80%, and an average pore diameter of 2.0 $\mu$m at the inside surface and 150 $\mu$m at the outside surface.

A stainless steel wire having a diameter of 0.4 mm was inserted through the wall of the tubing at a position 5 mm from one end, and made into a loop form. When the stainless steel loop was pulled at a speed of 50 mm/min in the axial direction, tearing occurred in the tubing at a load of 3,800 g, which was far larger than the load of 180 g which was the result obtained with a tubing produced by performing ordinary sintering. This shows that the orientation of the microfibrous structure of the PTFE tubing became strong around the tube axis which was a direction at right angles to the axial direction of the tubing.

When the tubing obtained in this Example was joined with the vessel of a patient, it was not torn, and its surface showed good ability to connect with the tissues of the patient. Thus, it had superior characteristics as a vascular prosthesis.

While the invention has been described in detail and with reference to specific embodiments thereof, it will be apparent to one skilled in the art that various changes and modifications can be made therein without departing from the spirit and scope thereof.

What is claimed is:

1. A unitary porous structure of polytetrafluoroethylene having a microfibrous structure composed of fibers and nodes connected to one another by these fibers, said microfibrous structure having at one surface a strong orientation of fiber in one direction and at another surface a strong orientation of nodes sintered by means of heating above 327° C. resulting in melt-adhesion of the nodes connected to one another in a direction at right angles to the aforesaid direction, the orientation of said microfibrous structure progressively changing from one surface to the other.

2. A porous tubing of polytetrafluoroethylene having a microfibrous structure composed of fibers and nodes connected to one another by these fibers, the average pore diameter of the outside surface of said tubing being larger than that of its inside surface, and said fibrous structure changing progressively within the wall of the tubing from its inside surface in which the fibrous structure has a strong orientation of fibers in the axial direction of the tubing to its outside surface in which the fibrous structure has a strong orientation of nodes sintered by means of heating above 327° C. resulting in melt-adhesion of the nodes connected to one another around the axis of the tubing.

3. The porous tubing of claim 2, wherein the inside surface of the tubing has an average pore diameter of about 1 to 100 μm, and the outside surface has an average pore diameter of about 0.1 to 1.0 mm.

4. A vascular prosthesis which is in the form of a porous tubing of polytetrafluoroethylene having a microfibrous structure composed of fibers and nodes connected to one another by these fibers, the average pore diameter of the outside surface of said tubing being larger than that of its inside surface, and said fibrous structure changing progressively within the wall of the tubing from its inside surface in which the fibrous structure has a strong orientation of fibers in the axial direction of the tubing to its outside surface in which the fibrous structure has a strong orientation of nodes sintered by means of heating above 327° resulting in melt-adhesion of the nodes connected to one another around the axis of the tubing.

5. A vascular prosthesis according to claim 4, wherein the inside surface of the tubing has an average pore diameter of about 1 to 100 μm, and the outside surface has an average pore diameter of about 0.1 to 1.0 mm.

6. The vascular prosthesis according to claim 4, wherein the tubing has an inside diameter of 4.0 mm and an outside diameter of 4.9 mm.

7. The vascular prosthesis according to claim 6, wherein the porous tubing has as average pore diameter of 2.0 μm at the inside surface and an average pore diameter of 150 μm at the outside surface.

8. The vascular prosthesis according to claim 7, wherein the porous tubing has a porosity of 80%.

9. The vascular prosthesis according to claim 4, wherein the porous tubing has a porosity of 80%.

10. A vascular prosthesis according to claim 6, wherein the inside surface of the tubing has an average pore diameter of about 1 to 100 μm, and the outside surface has an average pore diameter of about 0.1 to 1.0 mm.

11. A vascular prosthesis according to claim 9, wherein the inside surface of the tubing has an average pore diameter of about 1 to 100 μm, and the outside surface has an average pore diameter of about 0.1 to 1.0 mm.

* * * * *